United States Patent [19]

Ogura

[11] Patent Number: 4,855,592
[45] Date of Patent: Aug. 8, 1989

[54] APPARATUS USING OPTICAL FIBERS FOR INSPECTING SLIDE FASTENER ELEMENTS

[75] Inventor: Toyosaku Ogura, Kurobe, Japan

[73] Assignee: Yoshida Kogyo K. K., Tokyo, Japan

[21] Appl. No.: 228,537

[22] Filed: Aug. 5, 1988

[30] Foreign Application Priority Data

Aug. 10, 1987 [JP] Japan .............................. 62-122402[U]

[51] Int. Cl.⁴ .............................................. B21D 53/52
[52] U.S. Cl. .................................. 250/227; 250/561; 29/410; 29/705; 29/769
[58] Field of Search ................... 250/227, 561; 29/410, 29/705, 710, 766, 769; 24/381

[56] References Cited

U.S. PATENT DOCUMENTS

| | | | |
|---|---|---|---|
| 4,365,403 | 12/1982 | Ooura | 29/766 |
| 4,443,924 | 4/1984 | Osaki | 29/410 |
| 4,457,062 | 7/1984 | Osaki | 29/766 |
| 4,60,4783 | 8/1986 | Kojima et al. | 29/766 |
| 4,619,141 | 10/1986 | Yoshieda | 73/865.9 |
| 4,625,375 | 12/1986 | Osaki | 29/766 |

FOREIGN PATENT DOCUMENTS 59-32124 8/1984 Japan .
61-94606 5/1986 Japan .

Primary Examiner—David C. Nelms
Assistant Examiner—Stephone B. Allen
Attorney, Agent, or Firm—Hill, Van Santen, Steadman & Simpson

[57] ABSTRACT

Apparatus for inspecting irregular coupling elements from continuously running slide fastener chains is essentially comprised of a light source including a light emitter and a light receptor, an optical fiber extending from the light source and having a leading end arranged to face a row of coupling elements along their rounded corners, and a comparator connected to the light source. The light emitter cooperates with the optical fiber in emitting light rays onto the coupling elements, and the light receptor receives via the optical fiber light rays reflected from the rounded corners and converts the reflected rays to electrical signals. The comparator successively compares the signals to the reference standard to detect irregular coupling elements.

4 Claims, 2 Drawing Sheets

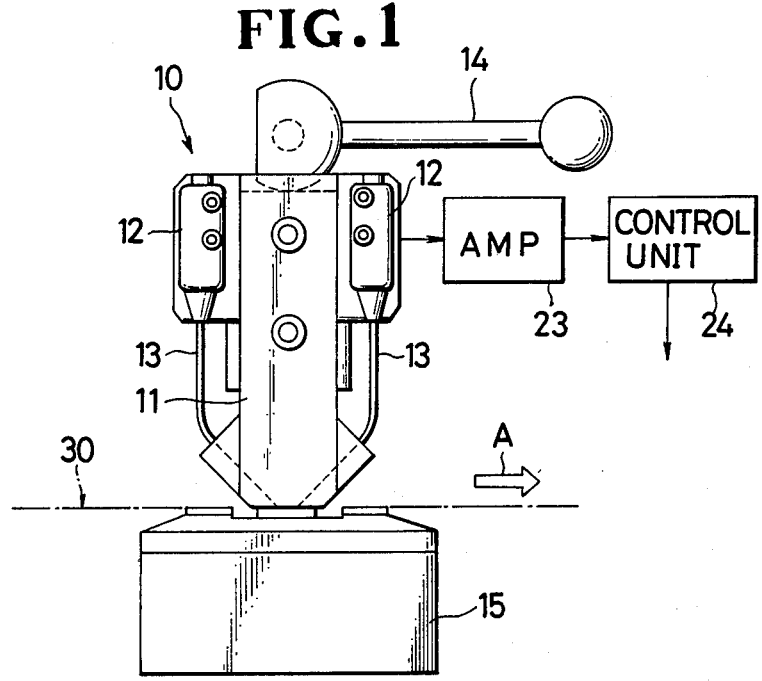
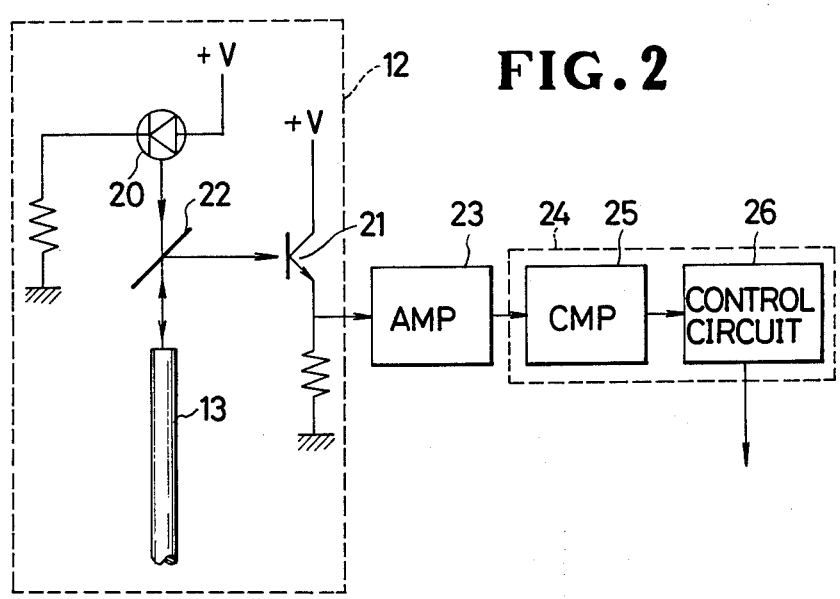

APPARATUS USING OPTICAL FIBERS FOR INSPECTING SLIDE FASTENER ELEMENTS

BACKGROUND OF THE INVENTION

1. Field of the Invention

This invention relates to apparatus for inspecting malformed coupling elements from slide fastener chains.

2. Prior Art

Coupling elements of a discrete type are susceptible to malformation or otherwise irregularity while in corner rounding. These problems are due to tension being not constantly applied onto a slide fastener chain passing through a chamfering device. In such instance, the coupling elements tend to disposed in that device, leading to excessive rounding at either one corner portion. Acceptable coupling elements have their corners rounded at a uniformly slight travel.

Certain apparatus have been proposed to detect malformed coupling elements. One such apparatus is directed to visually inspecting finished slide fasteners as disclosed for instance in Japanese Patent Publication No. 61-94606. This prior apparatus, however, is not wholly satisfactory from the accuracy point of view because visual inspection varies with the operator's skill and concentration and also with his or her fatique, sometimes inviting oversights. Detecting slide fastener products one at a time entails labors and time burdens. Japanese Patent Laid-Open Publication No. 59-32124 teaches an optical inspection with use of laser beams which however calls for costly, spacious apparatus.

SUMMARY OF THE INVENTION

With the foregoing difficulties of the prior art in view, the present invention seeks to provide new and improved apparatus for inspecting the malformation of coupling elements from slide fastener chains which is less costly and rather simple to construct and highly reliable to detect.

To be more specific, the apparatus according to the invention contemplates optically detecting irregular coupling elements by the use of light emitter and receptor units combined with optical fibers. The apparatus is suitable particularly for use with continuously running slide fastener chains.

Other objects and advantages of the invention will be better understood from the following description read with reference to the accompanying drawings in which a preferred embodiment of the invention is shown for illustrative purposes.

According to the invention, there is provided apparatus for inspecting the malformation of coupling elements from slide fastener chains, which comprises (a) a holder, (b) at least one light source carried on the holder and including light emitter means and light receptor means, (c) at least one optical fiber extending from the light source and having a leading end arranged to face a row of coupling elements along the chamfered corners, and (d) a comparator connected to the light source, whereby the light emitter means emits through the optical fier light rays onto the row of coupling elements, the light receptor means receives via the optical fiber light rays reflected from the chamfered corners and converts the reflected rays to pulse signals, and the comparator compares the resulting signals with the reference standard thereby detecting irregular coupling elements.

BRIEF DESCRIPTION OF THE DRAWINGS

FIG. 1 is a front elevation of the apparatus embodying the present invention;

FIG. 2 is a diagrammatic representation of an electrical circuit practical for use in the apparatus;

DETAILED DESCRIPTION OF THE INVENTION

Figure 3:
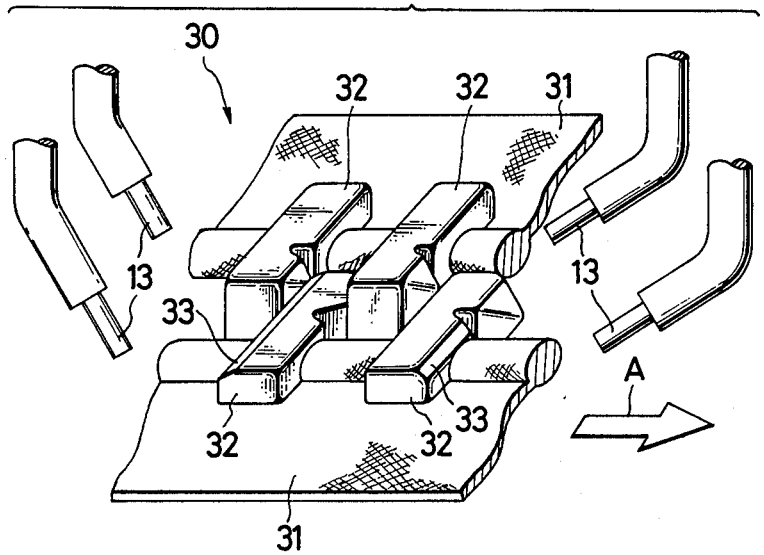
FIG. 3 is a partly enlarged, perspective view showing the manner in which a plurality of optical fibers are positioned relative to two rows of coupling elements.

Referring to the drawings and in particular to FIG. 1, there is shown apparatus 10 constructed in accordance with the present invention. The apparatus 10 comprises a vertically disposed holder 11 and a light source 12 carried thereon at their upper sides and including a light emitter unit and a light receptor unit. Light emitter units useful for the purpose of the invention include a light emitting diode and the like, and suitable light receptor units include a phototransistor and the like.

Two pairs of spaced apart optical fibers 13, 13, which are arranged to extend downwardly from the light source 12, are inwardly angled 45 degrees and secured opposite to each other at a lower portion of the holder 11. The paired optical fibers 13, 13, as shown in FIG. 3, have their respective leading ends positioned to be in face-to-face relation with the rounded corners of coupling elements. This positioning allows two interengaged rows of coupling elements to be simultaneously inspected.

A slide fastener chain to be inspected is made up of a pair of stringer tapes 31 and two intermeshed rows of discrete coupling elements 32 attached onto one longitudinal edge portion thereof. Designated at 33 in FIG. 3 are coupling elements corner resulting from excessive chamfering.

The optical fibers 13 each are connected to one light source. Four light sources 12 are employed in this embodiment, only two of which are seen from FIG. 1.

Figure 4:
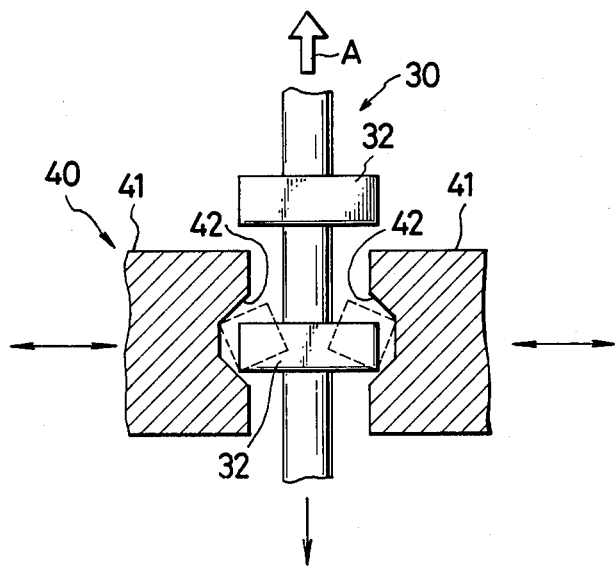
FIG. 4 is a segmentary, vertical cross-sectional view of a chambering device in which a certain pair of coupling elements are shown to have mismatched with two opposite chamfering recesses.

In FIG. 4 a chamfering device 40 is constructed with two oppositely disposed, horizontally movable hammers 41. Formed in the confronting surfaces of the hammers 41 are recesses 42 to chamfer the coupling elements 32. FIG. 4 is explanatory of a certain intermeshed pair of coupling elements having become displaced out of the recesses 42, resulting in one corner being excessively rounded.

Angling of the optical fibers 13 at 45 degrees, as referred to above, is so determined as to be coaxial with the axis of the recesses 42.

FIG. 2 shows a typical electrical circuit for use in the apparatus 10. Built in the light source 12 are as the light emitter unit a light emitting diode (LED) 20 located remote from and opposite to the connecting end of the optical fiber 13, and as the light receptor unit a phototransistor 21 arranged to receive via a half mirror 22 light rays from the optical fiber 13. The output of the transistor 21 is transferred through a gain control amplifier (AMP) 23 to a comparator (CMP) 25 of a control unit 24, the comparator 25 acts to determine pulse arrays of pulse signals resulting from light rays reflected from the rounded corners of the coupling elements 32 and converted by the transistor 21. The system of calculation and display is optional and may be selected from a digital computation in which each pulse width is counted to compare the resulting counts with the reference standard, or form an analog computation in which each pulse is integrated to compare the resulting integrates with the reference standard.

Advantageously, the apparatus according to the invention enables the inspection of a slide fastener chain that is a semi-finished slide fastener. The apparatus 10 is generally mounted on a base 15 for up and down movement by a lever 14 between operative and inoperative positions. The direction of feed of the slide fastener chain 30 is indicated by an arrow A in FIG. 1.

In operation, the slide fastener chain is allowed to continuously run through the apparatus 10 so as to simultaneously inspect two intermeshed rows of coupling elements 32. A narrow pulse width of reflected light rays is provided from acceptably rounded coupling elements, whereas a wide pulse width is obtained from light rays reflected from coupling elements of excessive chamfering as shown at 33 in FIG. 3. These reflected light rays are received and converted by the transistor 21 to electrical signals which are subsequently transferred to the comparator 25. The resulting pulse width is then compared to the reference standard. Upon sensing of a pulse width wider than the standard, the comparator 25 relays to the control circuit 26 a signal that a malformed coupling element has occurred, after which the control circuit 26 outputs, providing a predetermined indication of malformation.

The optical inspection contemplated under the invention may be effected with respect to the coupling element rows only on a surface side. The chamfering device 40 is structured to round the coupling elements on surface and reverse sides so that one coupling element when mismatched with the recess 42 is objectionably chamfered on both sides.

There is no particular restriction imposed upon the number and positioning of optical fibers and the kind and configuration of light emitter and receptor units.

Having thus described the invention, it will be apparent to those skilled in the art that various changes and modifications may be made without departing from the scope of the appended claims.

What is claimed is:

1. Apparatus for inspecting the malfunction of coupling elements from slide fastener chains, which comprises:
   (a) a holder;
   (b) at least one light source carried on said holder and including light emitter means and light receptor means;
   (c) at least one optical fiber extending from said light source and having a leading end arranged to face a row of coupling elements along the chamfered corners; and
   (d) a comparator connected to said light source, whereby said light emitter means emits through said optical fiber light rays onto said row of coupling elements, said light receptor means receives via said optical fiber light rays reflected from the chamfered corners and converts the reflected rays to pulse signals, and said comparator compares the resulting signals with the reference standard thereby detecting irregular coupling elements.

2. Apparatus according to claim 1 wherein said light emitter means is a light emitting diode.

3. Apparatus according to claim 1 wherein said light receptor means is a phototransistor.

4. Apparatus according to claim 1 wherein a plurality of optical fibers are disposed in pair and opposite to each other.

* * * * *